United States Patent
Jolink et al.

(10) Patent No.: US 10,201,178 B2
(45) Date of Patent: Feb. 12, 2019

(54) STABLE LIQUID LACTASE COMPOSITIONS

(71) Applicant: DSM IP Assetss B.V., Heerlen (NL)

(72) Inventors: Fenna Johanna Catharina Jolink, Echt (NL); Albert Schaap, Echt (NL)

(73) Assignee: DSM IP ASSETS B.V., Heerlen (NL)

(*) Notice: Subject to any disclaimer, the term of this patent is extended or adjusted under 35 U.S.C. 154(b) by 0 days.

(21) Appl. No.: 15/122,625

(22) PCT Filed: Mar. 5, 2015

(86) PCT No.: PCT/EP2015/054652
§ 371 (c)(1),
(2) Date: Aug. 30, 2016

(87) PCT Pub. No.: WO2015/132349
PCT Pub. Date: Sep. 11, 2015

(65) Prior Publication Data
US 2017/0064989 A1 Mar. 9, 2017

(30) Foreign Application Priority Data

Mar. 5, 2014 (EP) .................................. 14157897

(51) Int. Cl.
*A23L 33/00* (2016.01)
*A23L 33/195* (2016.01)
*A23L 2/66* (2006.01)
*A61K 38/47* (2006.01)
*C12N 9/38* (2006.01)

(52) U.S. Cl.
CPC ................ *A23L 33/40* (2016.08); *A23L 2/66* (2013.01); *A23L 33/195* (2016.08); *A61K 38/47* (2013.01); *C12N 9/2468* (2013.01); *C12Y 302/01023* (2013.01); *C12Y 302/01108* (2013.01); *A23V 2002/00* (2013.01)

(58) Field of Classification Search
CPC .......... A23L 2/66; A23L 33/195; A23L 33/40; A23V 2002/00; A61K 38/47; A61K 2300/00; A61K 31/355; A61K 31/375; A61K 31/445; A61K 31/7008; A61K 31/737; A61K 36/48; A61K 36/68; A61K 36/87; A61K 36/899; A61K 31/137; A61K 8/4973; A61K 9/0078; A61K 31/192; C12N 9/2468; C12Y 302/01023; C12Y 302/01108

See application file for complete search history.

(56) References Cited

U.S. PATENT DOCUMENTS 8,298,596 B2 * 10/2012 Solomon .............. A23C 9/1206
426/587

FOREIGN PATENT DOCUMENTS

| CN | 1916170 A | 2/2007 |
|---|---|---|
| CN | 100497613 C | 6/2009 |
| CN | 102550922 A | 7/2012 |
| CN | 102599606 A | 7/2012 |
| GB | 1306751 A | 2/1973 |
| JP | S58 107178 A | 6/1983 |
| WO | 02/081673 A1 | 10/2002 |
| WO | 2006/087409 A1 | 8/2006 |
| WO | 2013/084244 A1 | 6/2013 |

OTHER PUBLICATIONS

R.R. Mahoney et al.; "Stabilization of Lactase )*Escherichia coli*) by Milk Components and Related Compounds"; Journal of Food Science; Jul./Aug. 1989; vol. 54; No. 4; Chicago, IL, US; pp. 899-901.
Wayne G. Geilman et al.; "Production of an Electrolyte Beverage from Milk Permeate"; Journal of Dairy Science; Sep. 1992; vol. 75; No. 9, Champaign, IL, US; pp. 2364-2369.
Gabriela Zarate et al.; "Some Characteristics of Practical Relevance of the β-Galactosidase from Potential Probiotic Strains of Propionibacterium acidipropionici"; Anaerobe; 2002; vol. 8; pp. 259-567.
International Search Report of International Patent Application No. PCT/EP2015/054652 dated May 19, 2015.

* cited by examiner

*Primary Examiner* — Deborah K Ware
(74) *Attorney, Agent, or Firm* — McBee Moore Woodward & Vanik IP, LLC; Susan McBee; Chester Moore

(57) ABSTRACT

A stable aqueous liquid lactase formulation is provided, comprising lactase and further comprising sodium, calcium or potassium-L-lactate or a combination thereof and optionally a sugar, and/or optionally comprising sodium or potassium chloride or a combination thereof, preferably wherein the concentration of each of the components is such that the water activity $A_w$ is at most 0.82. The formulation is particularly suitable when using invertase-free lactase, allowing the use of sucrose as stabilizer. Also provided is a process to produce the liquid lactase formulation, an infant formula (e.g. as powder of granulate) comprising the liquid lactase formulation, a method to produce said infant formula, and the use of the formulation in the production of infant formula.

20 Claims, No Drawings

STABLE LIQUID LACTASE COMPOSITIONS

CROSS REFERENCE TO RELATED APPLICATIONS

This application is a § 371 National Stage Application of PCT/EP2015/054652, filed Mar. 5, 2015, which claims priority to EP14157897.1, filed Mar. 5, 2014.

FIELD OF THE INVENTION

The invention relates to a liquid lactase formulation, a process for the production thereof, a process to produce an infant formula, follow-on or toddler, an infant, follow-on or toddler formula comprising a lactase formulation, and the use of the formulation in the production of infant, follow-on or toddler formula.

BACKGROUND OF THE INVENTION

Lactase or β-galactosidase (E.C: 3.2.1.23) is an enzyme which catalyses the hydrolysis of lactose (a disaccharide) into its component monosaccharides glucose and galactose. Lactose is present in dairy products and more specifically in milk, skimmed milk, cream, yoghurt, ice-cream and other milk products.

In juveniles and people that are lactose tolerant, lactose is hydrolyzed into galactose and glucose by the "lactase-phlorizin hydrolase" (LPH) in the small intestinal brush border of the jejunum. LPH is encoded by a single lactase gene LCT in humans, and it is found that the ability to digest lactose in adulthood is due to cis-acting mutations in gene expression and inherited in a dominant manner. Lactose, in contrast to the mono-sugars (i.e., glucose and galactose), is poorly absorbed in the small intestine. People that do not carry mutations in the LCT gene will not digest and absorb lactose, and malabsorbed lactose will osmotically attract fluid into the bowel lumen which will lead to a loose stool. Additionally, lactose is a substrate for intestinal bacteria in the colon that metabolize it, producing volatile fatty acids and gases such as carbon dioxide, hydrogen and methane, leading to flatulence and cramping. Current estimate is that only 25-30% of the world population carries the mutation in the LCT gene and is also at adulthood able to digest lactose in the small intestine. The rest of the world population has varying difficulty with lactose digestion and this often leads to reduced intake of dairy products. Such individuals are called "lactose intolerant". Since dairy products are an important component of a healthy diet, due to the presence of several vitamins, proteins and minerals, this is an unwanted situation.

Lactases have been described for and isolated from a large variety or organisms, including micro-organisms. Lactase is often an intracellular component of micro-organisms like *Kluyveromyces* and *Bacillus*. *Kluyveromyces* and especially *K. fragilis*, *K. marxianus* and *K. lactis*, and other yeasts such as those of the genera *Candida, Torula* and *Torulopsis* are a common source of yeast lactases, whereas *B. coagulans* or *B circulans* are well known sources for bacterial lactases. Several commercial lactase preparations, derived from these organisms are available such as Maxilact (from *K. lactis*, produced by DSM, Delft, the Netherlands). All these lactases are so called neutral lactases since they have a pH optimum between pH=6 and pH=8. Several organisms such as *Aspergillus niger* and *Aspergillus oryzae* can produce extracellular lactase, and U.S. Pat. No. 5,736,374 describes an example of such lactase, produced by *Aspergillus oryzae*.

The enzymatic properties of lactases like pH- and temperature optimum vary between species. In general, however, lactases that are excreted show a lower pH-optimum of pH=3.5 to pH=5.0 (acid lactases); intracellular lactases usually show a higher pH optimum in the region of pH=6.0 to pH=7.5 for neutral lactases, but exceptions on these general rules occur.

Currently, lactase is formulated and commercially sold as a liquid. Two factors are of great importance when producing a liquid formulation, namely microbial and enzymatic stability. With microbial stability is meant that the liquid formulation stays free of microorganisms, or at least that growth is prevented or slowed down.

Several liquid lactase products are currently on the market. Examples of these (neutral lactases only) are Lactozym Pure 6500 L, sold by Novozymes; Ha-Lactase 5200, sold by Chr. Hansen; GODO YNL-2, sold by DuPont-Danisco; and Maxilact LGX 5000 and LGi, both sold by DSM Food Specialties. All the above products, and indeed all liquid lactase formulations presently on the market contain approximately 50% glycerol. It has been found that glycerol both affords good microbial and enzymatic stabilization. The amount of glycerol is such that the water activity (Aw) is at most 0.82. This prevents microbiological growth. In addition, the glycerol also affords enzymatic stability. A typical strength of a commercial lactase solution is about 1000, 2000 or 5000 NLU/g. The term NLU/g refers to the amount of lactase activity per gram end product.

An important industrial application of lactase is in the production of lactose-hydrolyzed milk products for lactose intolerant individuals. Such hydrolysed milk products include pasteurized milk, UHT-milk, milk reconstituted from all or part of its original constituents with or without intermediate processing steps such as protein hydrolysis, and infant formula.

A particularly interesting application of lactase is infant, follow-on or toddler formula. Infant formula is a manufactured food designed and marketed for feeding to babies and infants under 12 months of age, usually prepared for bottle-feeding or cup-feeding from powder (mixed with water) or liquid (with or without additional water). The U.S. Federal Food, Drug, and Cosmetic Act (FFDCA) defines infant formula as "a food which purports to be or is represented for special dietary use solely as a food for infants by reason of its simulation of human milk or its suitability as a complete or partial substitute for human milk". The most commonly used infant formulas contain purified cow's milk whey and casein as a protein source, a blend of vegetable oils as a fat source, lactose as a carbohydrate source, a vitamin-mineral mix, and other ingredients depending on the manufacturer.

A problem with currently available lactase formulations is that in many countries the addition or carry-over of glycerol to infant, follow-on or toddler formula is prohibited by law. This makes the present lactase formulations, which all contain glycerol, unsuitable to produce infant, follow-on or toddler formula. Therefore, there is a need for stable liquid lactase formulations which are suitable for infant, follow-on or toddler formula and substantially free of glycerol.

SUMMARY OF THE INVENTION

The invention provides stable aqueous liquid lactase formulations which are suitable for use in infant, follow-on or toddler formula and are free of glycerol. The stable lactase formulations comprise at least 20 wt % sodium, calcium or potassium-L-lactate or a combination thereof, preferably wherein the concentration of each of the components is such that the water activity $A_w$ is at most 0.82. An example of an optional component in such a formulation is a sugar. Another example of an optional component in such a formulation is sodium or potassium chloride or a combination thereof. An example of combined optional components in such a formulation is sodium or potassium chloride or a combination thereof as well as a sugar. The formulations are particularly suitable when using invertase-free lactase, allowing the use of sucrose as stabilizer. The invention also provides a process to produce the liquid lactase formulations of the invention, an infant, follow-on or toddler formula (e.g. as powder of granulate) comprising the liquid lactase formulations of the invention, a method to produce said infant, follow-on or toddler formula, and the use of the formulations in the production of infant, follow-on or toddler formula.

DETAILED DESCRIPTION OF THE INVENTION

The term "a" or "an" as used herein is defined as "at least one" unless specified otherwise. When referring to a noun (e.g. a compound, a cell etc.) in the singular, the plural is meant to be included.

In a first aspect, the invention provides an aqueous liquid lactase formulation, comprising lactase and further comprising at least 20 wt % sodium, calcium or potassium-L-lactate or a combination thereof preferably wherein the concentration of each of the components is such that the water activity $A_w$ is at most 0.82. Preferably, the invention provides an aqueous liquid lactase formulation comprising lactase and further comprising at least 20 wt % sodium, calcium or potassium-L-lactate or a combination thereof, wherein the concentration of each of the components is such that the water activity $A_w$ is at most 0.82.

In a preferred embodiment, the invention provides an aqueous liquid lactase formulation, comprising lactase and further comprising at least 20 wt % sodium, calcium or potassium-L-lactate or a combination thereof and further comprising a sugar, preferably wherein the concentration of each of the components is such that the water activity $A_w$ is at most 0.82. Preferably, the invention provides an aqueous liquid lactase formulation comprising lactase and further comprising at least 20 wt % sodium, calcium or potassium-L-lactate or a combination thereof and further comprising a sugar, wherein the concentration of each of the components is such that the water activity $A_w$ is at most 0.82.

In a preferred embodiment, the invention provides an aqueous liquid lactase formulation, comprising lactase and further comprising at least 20 wt % sodium, calcium or potassium-L-lactate or a combination thereof and further comprising sodium or potassium chloride or a combination thereof, preferably wherein the concentration of each of the components is such that the water activity $A_w$ is at most 0.82. Preferably, the invention provides an aqueous liquid lactase formulation comprising lactase and further comprising at least 20 wt % sodium, calcium or potassium-L-lactate or a combination thereof and further comprising sodium or potassium chloride or a combination thereof, wherein the concentration of each of the components is such that the water activity $A_w$ is at most 0.82.

In a preferred embodiment, the invention provides an aqueous liquid lactase formulation, comprising lactase and further comprising at least 20 wt % sodium, calcium or potassium-L-lactate or a combination thereof and further comprising a sugar and further comprising sodium or potassium chloride or a combination thereof, preferably wherein the concentration of each of the components is such that the water activity $A_w$ is at most 0.82. Preferably, the invention provides an aqueous liquid lactase formulation comprising lactase and further comprising at least 20 wt % sodium, calcium or potassium-L-lactate or a combination thereof and further comprising a sugar and further comprising sodium or potassium chloride or a combination thereof, wherein the concentration of each of the components is such that the water activity $A_w$ is at most 0.82.

The inventors have surprisingly found that enzymatically stable liquid enzyme formulations are feasible without using glycerol. Preferably, said liquid enzyme formulation are also microbially stable. They found that lactase formulated as a liquid comprising at least 20 wt % sodium, calcium or potassium-L-lactate (preferably sodium-L-lactate) or a combination thereof and optionally a sugar and/or optionally comprising sodium or potassium chloride or a combination thereof and optionally whey protein, and having a water activity of at most 0.82, the enzymatic stability was good. Moreover, the microbial stability was good as well. This is all the more surprising because lactase in itself is not very stable at all.

The enzymatic stability is a measure for the rate at which the activity of the enzyme decreases. The microbial stability is a measure for the rate at which micro-organisms can proliferate and grow in the composition.

The lactase formulation of the invention is preferably suitable for use in infant, follow-on or toddler formula. That is, the lactase formulation can be used in a process for the production of infant, follow-on or toddler formula. To this end, the lactase formulation of the invention is preferably substantially free of polyol or diols, more preferably free of glycerol and/or sorbitol. The amount of glycerol, preferably the amount of glycerol and sorbitol is preferably less than 45 wt %, less than 40 wt %, more preferably less than 35 wt %, less than 30 wt %, less than 25 wt %, more preferably less than 20 wt %, less than 15 wt %, even more preferably less than 10 wt %, less than 5 wt %. Most preferably the lactase is free of glycerol or any other polyol or diol.

A lactase formulation of the invention is preferably also free from compounds (preservatives) such as sorbate and/or benzoate and/or parabens (alkyl esters of para-hydroxybenzoate).

The components (i.e. the stabilizing agents such as sodium, calcium or potassium-L-lactate, sugar, sodium or potassium chloride) of the lactase formulation of the invention are added in an amount such that the water activity $A_w$ is at most 0.82. The water activities of the individual components are known by the skilled person, and are described in hand books. The skilled person will appreciate that the amounts of the components in the formulation can be varied and exchanged such that the water activity remains at most 0.82. The contribution to the water activity of the ensemble of the components is the sum of the contribution of the individual components, i.e. the effect is cumulative. As used herein the water activity refers to the value measured at 25° C. A relatively low water activity can contribute to achieve a desired microbial stability. In the context of the present patent application the term "water activity" is used to formulate shelf-stable lactase formulations free from or low in glycerol or any other polyol or diol.

The term "aqueous liquid lactase formulation" encompasses any composition or solution comprising water, for instance at least 20 wt % of water, for instance at least 30 or 40 wt % of water.

A lactase formulation (or lactase preparation; the terms are used interchangeably herein) of the invention comprises at least 20 wt % sodium, calcium or potassium-L-lactate or a combination thereof. A lactase formulation can thus comprise at least 20 wt % sodium-L-lactate or at least 20 wt % calcium-L-lactate or at least 20 wt % potassium-L-lactate or a combination thereof such as at least 20 wt % sodium-L-lactate and calcium-L-lactate or at least 20 wt % sodium-L-lactate and potassium-L-lactate or at least 20 wt % calcium-L-lactate and potassium-L-lactate or at least 20 wt % sodium-L-lactate and calcium-L-lactate and potassium-L-lactate. In case of a combinations of lactates, the feature of "at least 20 wt %" refers to the combined concentrations of the individual L-lactates.

Sodium lactate is the sodium salt of lactic acid. Calcium lactate and potassium lactate are the respective calcium and potassium salt of lactic acid. In general, lactates such as sodium, calcium, and potassium lactate are salts derived from the neutralization of lactic acid and most commercially used lactic acids are fermented from dairy-free products such as cornstarch, potatoes, or molasses Sugar or tapioca additionally may be used. However some lactic acid is fermented from dairy products such as whey and lactose. Whey is made of up 6.5% solids of which 4.8% is solid lactose. Waste whey typically is used to produce lactic acid when the whey itself is produced as waste during the manufacture of certain dairy products.

Sodium, calcium or potassium-lactate can be present in D, L or DL form. Preferably, the L form is exclusively used. However, reference to sodium, calcium or potassium-L-lactate does not exclude the presence of minor amounts of for example sodium, calcium or potassium-D (or DL)-lactate. Minor amounts of the D-form of the sodium, calcium or potassium are amounts lower or equal to 5% of the total lactate, preferably lower or equal to 3% of the total lactate of the D-form being present in a stock of the L-form. Preferably, the used L-lactate is sodium-L-lactate.

The lactase formulation of the invention may, besides a lactase and at least 20 wt % sodium, calcium or potassium-L-lactate or a combination thereof, further comprise a sugar. Preferably said sugar is sucrose, fructose, glucose or lactose, or a combination thereof, more preferably said sugar is sucrose. The concentration of the used L-lactate and the sugar should be selected such that the water activity $A_w$ is at most 0.82. The skilled person is able to determine suitable concentrations without any undue burden. Fructose is only used for lactase preparations which are used in follow-on or toddler formula.

A lactase formulation of the invention may, besides a lactase and at least 20 wt % sodium, calcium or potassium-L-lactate or a combination thereof, further comprise sodium or potassium chloride or a combination thereof. Again, the respective concentrations are chosen such that the water activity $A_w$ is at most 0.82. The skilled person is able to determine suitable concentrations without any undue burden.

The lactase formulation of the invention may further comprise protein, preferably whey protein. The amount of whey protein in the liquid formulation is preferably between 1 and 15 g/l, measured as beta-lactoglobulin, more preferably between 3 and 12 g/l, more preferably between 4 and 6 g/l.

The lactase in the formulation is preferably a neutral lactase. The concentration of lactase, preferably neutral lactase in the formulation of the invention may be anywhere between 500 and 15000 NLU/g, and is typically 1000, 2000 or 5000 NLU/g. The neutral lactase preferably is active, or has its optimal activity, at a pH between 6-9, preferably between pH 7-8 or more preferably pH 6.5-7.5.

The lactase activity is determined as Neutral Lactase Units (NLU) using o-nitrophenyl-β-D-galactopyranoside (ONPG) as the substrate, according to the procedure described in FCC (sixth ed, 2008, p 1124-1126: Lactase (neutral) β-galactosidase activity).

A lactase in a formulation of the invention is preferably an intracellular produced neutral lactase in which case the neutral lactase is extracted from its host cells by methods known to the skilled person.

Neutral lactases have been described and isolated from a large variety or organisms, including micro-organisms. Lactase is often an intracellular component of micro-organisms like *Kluyveromyces* and *Bacillus*. *Kluyveromyces* and especially *K. fragilis* and *K. lactis*, and other yeasts such as those of the genera *Candida, Torula* and *Torulopsis* are a common source of yeast lactases, whereas *B. coagulans, B. circulans* or lactic acid bacteria are well known sources of bacterial lactases. Several commercial lactase preparations, derived from these organisms are available such as Maxilact® (from *K. lactis*, produced by DSM, Delft, the Netherlands). Preferably, the lactase formulation of the invention comprises neutral *Kluyveromyces lactis* lactase and more preferably neutral *K. lactis* lactase.

The lactase in the formulation of the invention may be obtained as an optionally concentrated extract e.g. from *K. lactis*. Preferably such extract has undergone a solid-liquid separation step, by e.g. centrifugation or filtration, to remove the solids. Such a extract may contain natural components from the yeast as well as remainders of the fermentation media. Examples of such components are nucleic acid, protein, residual sugars, oligosaccharides, intrinsic enzymes. salts, minerals, intracellular components, ions, and nucleotides or other components. These components may end up, to some extent, in the formulation of the invention. For example, in a 5000 NLU/g lactase formulation the amount of protein, other than lactase, is typically between 0.1 and 10 wt % based in the total weight of the composition, more likely between 1 and 5 or 1 and 4, between 2 and 3 wt %. The amount of salts, ash, saccharides, nucleic acid etc in such formulation is typically between 0.5 and 4 wt %.

Alternatively, the lactase can be an acid lactase, i.e. a lactase having its pH optimum in the range between 3.5 to 5.0.

To avoid any confusion, the herein mentioned amounts of for example sodium, calcium or potassium-L-lactate or a sugar or sodium or potassium chloride (or any other added component) refers to the amount of added component and is not including the possible carry-over from components present in the lactase extract as described above.

Furthermore, the water activity $A_w$ also takes into account the water activity of the lactase solution (for example lactase extract or purified lactase preparation) which may slightly vary depending on the used batch.

The lactase in the formulation of the invention may be a concentrated (non-purified) lactase or may be purified. The concentrated (non-purified) lactase can be obtained by releasing the enzyme from the host cells, removing the solids for instance by means of filtration or centrifugation and by concentrating the liquid phase (lactase) by means of for instance ultrafiltration. Alternatively, the lactase is purified, for example by using chromatography.

The sugar in the liquid lactase formulation of the invention can include monosaccharides such as fructose or glucose; disaccharides such as lactose or sucrose, or oligosaccharides. Preferred sugars are soluble in water.

The lactase formulation of the invention is preferably substantially free from invertase. Invertase [EC 3.2.1.26] is an enzyme that catalyzes the hydrolysis of sucrose to form one monomer of glucose and one momomer of fructose. The resulting mixture of fructose and glucose is called inverted sugar syrup. Commercial lactase often contain traces of invertase. The inventors found that sucrose often does not give satisfactory results regarding the enzymatic stability of lactase. They surmised that the presence of invertase may be related to this problem. The inventors also found that glucose is less efficient as stabiliser than other sugars, which might be a possible explanation of the insufficient stabeliz-ing effect of sucrose. Indeed, they found that when a invertase-free lactase was used in the formulation of the invention, sucrose was an effective stabilizer for the enzyme stability. Thus, in a preferred embodiment the formulation of the invention comprises sucrose and substantially no inver-tase.

As descibed above, the invention provides an aqueous liquid lactase formulation, comprising lactase and further comprising at least 20 wt % sodium, calcium or potassium-L-lactate or a combination thereof. Such a formulation may optionally comprise
a sugar; or
sodium or potassium chloride or a combination thereof; or
sodium or potassium chloride or a combination thereof as well as a sugar preferably wherein the concentration of each of the components is such that the water activity $A_w$ is at most 0.82.

One suitable lactase formulation comprises at least 20 wt %, 21 wt %, 22 wt %, 23%, 24%, 25 wt %, 26 wt %, 27 wt %, 28 wt %, 29 wt %, 30 wt %, 31 wt %, 32 wt %, 33 wt %, 34 wt % or 35 wt % sodium, calcium or potassium-L-lactate (preferably sodium-L-lactate) or a combination thereof. Preferably such a lactase formulation comprises between 500 and 15000 NLU/g lactase.

A lactase formulation of the invention may essentially consist of lactase and sodium, calcium or potassium-L-lactate (preferably sodium-L-lactate) or a combination thereof. Alternatively, a lactase formulation may comprise (i) lactase, (ii) at least 20 wt % sodium, calcium or potas-sium-L-lactate or a combination thereof and (iii) a sugar. Preferably said sugar is sucrose, fructose, glucose or lactose, or a combination thereof, more preferably said sugar is sucrose.

Alternatively, a lactase formulation may comprise (i) lactase, (ii) at least 20 wt % sodium, calcium or potassium-L-lactate or a combination thereof and (iii) sodium or potassium chloride or a combination thereof.

Alternatively, a lactase formulation may comprise (i) lactase, (ii) at least 20 wt % sodium, calcium or potassium-L-lactate or a combination thereof, (iii) a sugar and (iv) sodium or potassium chloride or a combination thereof.

In all cases, the concentration of the individual compo-nents is selected such that the final water activity $A_w$ is at most 0.82.

The pH of a lactase formulation of the invention is in the range of pH 6-9, preferably pH 7-8.5, preferably pH 7-8.

One suitable lactase formulation comprises 1000, 2000, or 5000 NLU/g lactase and 25 wt %, 26 wt %, 27 wt %, 28 wt %, 29 wt %, 30 wt %, 31 wt %, 32 wt %, 33 wt %, 34 wt % or 35 wt % Na-L-lactate, preferably 5000 NLU/g lactase and 30 wt % Na-L-lactate.

Another preferred lactase formulation comprises 5000 NLU/g lactase, 30 wt % Na-L-lactate, and whey protein (5-10 g/l, preferably 5 g/l measured as beta-lactoglobulin).

Another suitable lactase formulation comprises 1000, 2000, or 5000 NLU/g lactase and 5 wt %, 6 wt %, 7 wt %, 8 wt %, 9 wt %, 10% wt %, 11 wt %, 12 wt %, 13 wt %, 14 wt % or 15 wt % NaCl and 35 wt %, 36 wt %, 37 wt %, 38 wt %, 39 wt %, 40%, 41 wt %, 42 wt %, 43 wt %, 44 wt % or 45 wt % sucrose, preferably 5000 NLU/g lactase, 10 wt % NaCl, and 40 wt % sucrose.

Another preferred lactase formulation comprises 5000 NLU/g lactase, 10 wt % NaCl, 40 wt % sucrose and whey protein (5-10 g/l, preferably 5 g/l measured as beta-lacto-globulin).

Another suitable lactase formulation comprises 1000, 2000, or 5000 NLU/g lactase and 5 wt %, 6 wt %, 7 wt %, 8 wt %, 9 wt %, 10% wt %, 11 wt %, 12 wt %, 13 wt %, 14 wt % or 15 wt % NaCl and 13 wt %, 14 wt %, 15 wt %, 16 wt %, 17 wt %, 18 wt %, 19 wt %, 20 wt %, 21 wt %, 22 wt % or 23 wt % Na-L-lactate, preferably 5000 NLU/g lactase, 10% wt % NaCl, and 18% wt % Na-L-lactate.

Another preferred lactase formulation comprises 5000 NLU/g lactase, 10% wt % NaCl, 18% wt % Na-L-lactate, and whey protein (5-10 g/l, preferably 5 g/l measured as beta-lactoglobulin).

Another suitable lactase formulation comprises 1000, 2000, or 5000 NLU/g lactase and 15 wt %, 16 wt %, 17 wt %, 18 wt %, 19 wt %, 20 wt %, 21 wt %, 22 wt %, 23 wt %, 24 wt % or 25 wt % fructose and 17 wt %, 18 wt %, 19 wt %, 20 wt %, 21 wt %, 22 wt %, 23 wt %, 24 wt %, 25 wt %, 26 wt % or 27 wt % Na-L-lactate, preferably 5000 NLU/g lactase, 20% wt % fructose, and 22 wt % Na-L-lactate.

Another preferred lactase formulation comprises 5000 NLU/g lactase, 20% wt % fructose, 22 wt % Na-L-lactate, and whey protein (5-10 g/l, preferably 5 g/l measured as beta-lactoglobulin).

Another suitable lactase formulation comprises 100, 2000, or 5000 NLU/g lactase and 20 wt %, 21 wt %, 22 wt %, 23 wt %, 24 wt %, 25 wt %, 26 wt %, 27 wt %, 28 wt %, 29 wt % or 30 wt % sucrose and 15 wt %, 16 wt %, 17 wt %, 18 wt %, 19 wt %, 20 wt %, 21 wt %, 22 wt %, 23 wt %, 24 wt % or 25 wt % Na-L-lactate, preferably 5000 NLU/g lactase, 25 wt % sucrose, and 20 wt % Na-L-lactate.

Another preferred lactase formulation comprises 5000 NLU/g lactase, 25 wt % sucrose, 20 wt % Na-L-lactate, and whey protein (5-10 g/l, preferably 5 g/l measured as beta-lactoglobulin).

Another suitable lactase formulation comprises 100, 2000, or 5000 NLU/g lactase and 15 wt %, 16 wt %, 17 wt %, 18 wt %, 19 wt %, 20 wt %, 21 wt %, 22 wt %, 23 wt %, 24 wt % or 25 wt % fructose and 15 wt %, 16 wt %, 17 wt %, 18 wt %, 19 wt %, 20 wt %, 21 wt %, 22 wt %, 23 wt %, 24 wt % or 25 wt % sucrose.

Another preferred lactase formulation comprises 5000 NLU/g lactase, 20 wt % sucrose, 20 wt % fructose, and whey protein (5-10 g/l, preferably 5 g/l measured as beta-lacto-globulin).

Some further examples of preferred compositions are described:

One preferred lactase formulation comprises between 500-8000 NLU/g lactase and at least 28, 29 or 30 wt % sodium, calcium or potassium-L-lactate or a combination thereof, preferably at least 31 wt % or 32 wt % or 32.5 wt % sodium, calcium or potassium-L-lactate or a combination thereof.

Another preferred lactase formulation comprises between 500-8000 NLU/g lactase and at least 28, 29 or 30 wt % sodium-L-lactate, preferably at least 31 wt % or 32 wt % or 32.5 wt % sodium-L-lactate.

Another preferred lactase formulation comprises between 500-8000 NLU/g lactase and at least 25 wt % sodium, calcium or potassium-L-lactate or a combination thereof and sodium or potassium chloride in a range of 0.01-5 wt %, preferably 0.01-3 wt %, more preferably 0.01-3 wt %, most preferably 0.01-2 wt %.

Another preferred lactase formulation comprises between 500-8000 NLU/g lactase and at least 25 wt % sodium-L-lactate and potassium chloride in a range of 0.01-5 wt %, preferably 0.01-3 wt %, more preferably 0.01-3 wt %, most preferably 0.01-2 wt %.

Another preferred lactase formulation comprises between 500-8000 NLU/g lactase and at least 25 wt % sodium-L-lactate and potassium chloride in a range of 0.01-3 wt %, preferably 0.01-2 wt %.

The formulation of the invention is enzymatically stable and preferably microbial and enzymatically stable. That is, the residual enzymatic activity in the formulation after 2 months of storage at 2-8° C. (e.g. 4° C.) is at least 80%, preferably at least 90%, more preferably at least 95%, even more preferably at least 99%. Likewise, the microbial stability is such that the total plate count is preferably less than 1000, colony forming units (CFU) per ml after storage for 2 months at 2-8° C. (e.g. at 4° C.), more preferably less than 500, more preferably less than 300, even more preferably less than 200, most preferably less than 100 CFU/ml.

The microbial properties of a composition of the invention can be expressed by the standard plate count, number of yeasts and number of moulds using well-defined standard procedures. For instance, the standard plate count can be 100 CFU (colony forming unit) in 1 ml, the yeast count can be 10 CFU in 1 ml and the mould count can be 10 CFU in 1 ml. As compositions are often stored prior to use, it is desirable that the plate count, number of yeasts and number of moulds remain below certain boundary values, for a period of at least 2 months.

As used herein, the yeast and moulds count is determined according to NEN-ISO 21527-2.

In a further aspect the invention provides a process to produce the liquid lactase formulation of the invention said process comprising adding lactase, sodium, calcium or potassium-L-lactase or a combination thereof and optionally sugar, and/or optionally sodium or potassium chloride or a combination thereof, and/or water and optionally mixing. The lactase in said process may be, or may be obtained from an optionally concentrated fermentation broth (after lysing the cells), e.g. from K. lactis. Alternatively, the lactase may be a purified lactase, for example a lactase purified by chromatography. The order of adding the lactase and other components is not critical. The process may include mixing in order to obtain a clear solution.

In a further aspect the invention provides an infant, follow-on or toddler formula comprising the liquid lactase formulation of the invention or the lactase composition produced by the process of the invention as described above. Said infant, follow-on or toddler formula is preferably a dry formulation e.g. in the form of a powder of granulate. The amount of lactose in the infant, follow-on or toddler formula of the invention is preferably less than 1 wt % lactose, preferably less than 0.5 wt %, more preferably less than 0.2 wt %, even more preferable less than 0.1 wt %, all based on the total weight of the infant, follow-on or toddler formula. An infant formula is a manufactured food designed and marketed for feeding to babies and infants under 12 months of age. A follow-on or toddler formulas are sold for ages 6 months to 2 years.

In yet another aspect the inventon provides a method to produce an infant formula, such as the infant formula of the invention, said process comprising adding the liquid lactase formulation to a milk concentrate and optionally other components such as minerals, vitamins, and fats; mixing and/or homogenizing; evaporation; and spray-drying. The order of adding the components is not critical. For example, the process may be done such that the lactase formulation is added to a (liquid) milk concentrate, to which already components such as minerals, vitamins, and fats have been added. Alternatively, such other components are added after adding of the lactase formulation. In another embodiment, the lactase formulation is added to other components and the mixture is then added to the concentrated milk. Mixing, homogenization, spray-drying and granulating are all done according to standard methods known in the art.

In yet another aspect the invention provides the use of the liquid lactase formulation of the invention in the production of infant formula.

The invention will now be elucidated with reference to the following examples without however being limited thereto.

EXAMPLES

Example 1 a Lactase Formulation Comprising 32.5 wt % Na-Lactate

Concentrated lactase extracted from the yeast *Kluyveromyces lactis* can be obtained using methods as described in the prior art (e.g. Rodrigues Pinho and Lopes Passos (2011) Journal of Food Biochemistry 35, 323-336) or any other method for extraction and concentration of lactase from *Kluyveromyces* described previously. To 280 gram of this concentrated (non-purified) lactase, with an activity of ~14000 NLU/g, 520 g Na-L-lactate (50 wt % stock solution) was added. This resulted in a 32.5 wt % Na-L-lactate formulation with an activity of 4950 NLU/g, a pH of 7.0 and a water activity of 0.815. The pH measurement was performed using 1% sample solutions in Ultra High Quality (UHQ) water. The water activity is measured by measuring the relative humidity above the sample at 25° C. until the Aw value is stable. The Aw value is considered stable if no change >0.001 Aw is detected for 4 minutes. The Aw value is determined with standard equipment.

Samples of approximately 1 gram of the formulation were stored at 5° C. for respectively 2, 4 and 8 weeks. After removing the samples from the test, they were visual observed and determined on activity.

After 8 weeks the residual enzymatic activity of the formulation is 94%.

| Week | Residual activity [%] | Visual appearance |
| --- | --- | --- |
| 0 | 100 | Clear light brown liquid |
| 2 | 94 | Clear light brown liquid |
| 4 | 89 | Clear light brown liquid |
| 8 | 94 | Clear light brown liquid |

Example 2 a Lactase Formulation Comprising 20 wt % Na-Lactate+25 wt % Sucrose

To 280 gram concentrated lactase, (concentrated (non-purified) lactase) with an activity of ~14000 NLU/g, 320 g Na-L-lactate (50 wt % solution) and 200 g sucrose was added. This resulted in a 20 wt % Na-L-lactate+25 wt % sucrose formulation with an activity of 5040 NLU/g, a pH of 7.0 and a water activity of 0.815. The pH measurement was performed using 1% sample solutions in Ultra High Quality (UHQ) water. The water activity is measured by measuring the relative humidity above the sample at 25° C.

until the Aw value is stable. The Aw value is considered stable if no change >0.001 Aw is detected for 4 minutes. The Aw value is determined with standard equipment.

Samples of approximately 1 gram of the formulation were stored at 5° C. for respectively 2, 4 and 8 weeks. After removing the samples from the test, they were visual observed and determined on activity.

After 8 weeks the residual enzymatic activity of the formulation is 82%.

| Week | Residual activity [%] | Visual appearance |
|---|---|---|
| 0 | 100 | Clear light brown liquid |
| 2 | 88 | Clear light brown liquid |
| 4 | 86 | Clear light brown liquid |
| 8 | 82 | Clear light brown liquid |

Example 3 Microbial Challenge Test of a Lactase Formulation Comprising (i) 32 wt % Na-L-lactate Formulation or (ii) 20 wt % Na-L-lactate+25 wt % Sucrose or (iii) 50 wt % Glycerol Formulation To 350 gram concentrated lactase (concentrated (non-purified) lactase), with an activity of ~13600 NLU/g, 650 g Na-L-lactate (50 wt % solution) was added. The pH was adjusted to pH 7.8 with NaOH. This resulted in a 32.5 wt % Na-L-lactate formulation with an activity of ~4760 NLU/g, and a water activity of 0.80.

To 400 gram concentrated lactase (concentrated (non-purified) lactase), with an activity of ~13600 NLU/g, 457 g Na-L-lactate (50 wt % solution) and 285 g sucrose was added. The pH was adjusted to pH 7.8 with NaOH. This resulted in a 20 wt % Na-L-lactate+25 wt % sucrose formulation with an activity of ~4760 NLU/g, and a water activity of 0.794.

As a reference to 400 gram concentrated lactase, with an activity of ~13600 NLU/g, 150 g water and 550 g glycerol was added. The pH was adjusted to pH 7.8 with NaOH. This resulted in a 50 wt % glycerol formulation with an activity of ~4945 NLU/g, and a water activity of 0.769.

The aim of this test was to compare the microbial stability of a 50% glycerol lactase composition with a lactase formulation of the invention. This was done by challenging the different formulations according to NEN-ISO 21527-2 with a standard or robust cocktail of yeasts or moulds. Such a standard cocktail comprises a selection of general, ubiquitous microorganisms that are likely to be present in (food) products, ingredients or industrial processes or installations. A robust cocktail is a selection of strains that can grow under challenging conditions.

A cocktail of standard moulds, robust moulds, standard yeasts or robust yeasts was added to the formulation, incubated at 8° C. and 25° C. and sampled after 0, 1, 2, 3 weeks and 1, and 2 months to determine the microbial growth.

After two months the lactate comprising formulations are more microbial stable than the glycerol formulation for standard & robust yeasts and robust moulds. The lactate comprising formulations are equally microbial stable as the glycerol formulation for standard moulds.

The invention claimed is:

1. A stable aqueous liquid lactase formulation comprising lactase and at least 20 wt % sodium-L-lactate, calcium-L-lactate, potassium-L-lactate, or a combination thereof, wherein the concentration of each of the components is such that the water activity $A_w$ is at most 0.82, and wherein said formulation is substantially free of polyols or diols, including glycerol.

2. The stable aqueous liquid lactase formulation according to claim 1, further comprising a sugar.

3. The stable aqueous liquid lactase formulation according to claim 1, further comprising sodium chloride, or potassium chloride, or a combination thereof.

4. The stable aqueous liquid lactase formulation according to claim 2 wherein said sugar is sucrose, fructose, glucose, lactose, or a combination thereof.

5. The stable aqueous liquid lactase formulation according to claim 1 wherein the lactase is a neutral lactase.

6. The stable aqueous liquid lactase formulation according to claim 1 wherein the aqueous liquid lactase formulation is substantially free of invertase.

7. The stable aqueous liquid lactase formulation according to claim 6 which further comprises sucrose.

8. The stable aqueous liquid lactase formulation of claim 1, further comprising whey protein.

9. The stable aqueous liquid lactase formulation of claim 1 which is further substantially free of sorbitol.

10. An infant, follow-on and/or toddler formula as powder of granulate, comprising the stable aqueous liquid lactase formulation of claim 1.

11. The infant, follow-on and/or toddler formula of claim 10, which is a dry formulation.

12. The infant, follow-on and/or toddler formula of claim 10, wherein lactose is present in an amount of less than 1 wt %, based on the total weight of the infant, follow-on or toddler formula.

13. A process to produce the stable aqueous liquid lactase formulation of claim 1 said process comprising adding and mixing:
    (a) lactase,
    (b) sodium-L-lactate, calcium-L-lactate, potassium-L-lactate, or a combination thereof, and
    (c) water.

14. The process of claim 13, further comprising adding and mixing:
    (d) sugar, sodium chloride, potassium chloride, or a combination thereof.

15. A method to produce an infant, follow-on or toddler formula comprising:
    (a) adding the stable aqueous liquid lactase formulation of claim 1 to a milk concentrate;
    (b) mixing; or homogenizing;
    (c) evaporating; and
    (d) spray-drying.

16. The method of claim 15, further comprising granulating.

17. The method of claim 15, further comprising adding minerals, vitamins, fats, or combinations thereof to: the stable aqueous liquid lactase formulation; the milk concentrate; or the milk concentrate to which the stable aqueous liquid lactase formulation has been added.

18. A stable aqueous liquid lactase formulation consisting essentially of
    (i) lactase and at least 20 wt % sodium-L-lactate, calcium-L-lactate,-potassium-L-lactate, or a combination thereof,
    (ii) sugar; and
    (iii) whey protein,
    (iii) sodium chloride, or potassium chloride, or a combination thereof,
    wherein the concentration of each of the components is such that the water activity $A_w$ is at most 0.82, wherein said formulation is substantially free of polyols or diols, including glycerol, and wherein the formulation is suitable for administration to infants and toddlers.

19. An infant, follow-on and/or toddler formula as powder of granulate, comprising the stable aqueous liquid lactase formulation of claim 18.

20. The stable aqueous liquid lactase formulation according to claim 19 wherein said sugar is sucrose, fructose, glucose, lactose, or a combination thereof.

* * * * *